United States Patent
Lindeman et al.

(10) Patent No.: US 11,622,685 B2
(45) Date of Patent: Apr. 11, 2023

(54) REMOTE EQUIPMENT MONITORING SYSTEM

(71) Applicant: Cornell Pump Company, Clackamas, OR (US)

(72) Inventors: Adam Lindeman, Portland, OR (US); Andrew Enterline, Troutdale, OR (US); Marcus Davi, Portland, OR (US)

(73) Assignee: Cornell Pump Company LLC, Wilmington, DE (US)

( * ) Notice: Subject to any disclaimer, the term of this patent is extended or adjusted under 35 U.S.C. 154(b) by 382 days.

(21) Appl. No.: 16/855,031

(22) Filed: Apr. 22, 2020

(65) Prior Publication Data
US 2020/0337558 A1 Oct. 29, 2020

Related U.S. Application Data

(60) Provisional application No. 62/840,025, filed on Apr. 29, 2019.

(51) Int. Cl.
*G16H 40/67* (2018.01)
*A61B 5/00* (2006.01)

(52) U.S. Cl.
CPC .......... *A61B 5/0022* (2013.01); *G16H 40/67* (2018.01); *A61B 2560/0204* (2013.01); *A61B 2562/0219* (2013.01); *A61B 2562/0247* (2013.01); *A61B 2562/0271* (2013.01)

(58) Field of Classification Search
CPC .......... A61B 5/0022; A61B 2560/0204; A61B 2562/0219; A61B 2562/0247; A61B 2562/0271; G16H 40/67
See application file for complete search history.

(56) References Cited

U.S. PATENT DOCUMENTS

| 6,138,078 A | 10/2000 | Canada et al. |
| 8,154,417 B2 | 4/2012 | Hauenstein et al. |
| 9,127,678 B2 | 9/2015 | Gomez et al. |

(Continued)

FOREIGN PATENT DOCUMENTS

| CN | 206162152 U | 5/2017 |
| CN | 207879579 U | 9/2018 |

(Continued)

OTHER PUBLICATIONS

International Search Report and Written Opinion issued in corresponding International Application No. PCT/US2020/029194 dated Jul. 8, 2020, 14 pages.

*Primary Examiner* — Mohamed Charioui
*Assistant Examiner* — Christine Y Liao
(74) *Attorney, Agent, or Firm* — Snyder, Clark, Lesch & Chung, LLP

(57) ABSTRACT

A device, system, and methods are provided for remotely monitoring pump equipment. A monitoring device is mechanically mounted to a pump. The monitoring device includes internal vibration, temperature, and location sensors to periodically monitor a pump and upload data samples via cellular connection to a provider network. The monitoring device additionally includes connections to external sensors that can be sampled and uploaded with the other data samples, when the monitoring device is connected to external power. Authenticated users access the pump data though a user device that connects to the provider network.

20 Claims, 11 Drawing Sheets

(56) References Cited

U.S. PATENT DOCUMENTS

| | | |
|---|---|---|
| 2014/0028462 A1 | 1/2014 | Lawson |
| 2017/0170979 A1* | 6/2017 | Khalid ................ H04L 12/2818 |
| 2017/0205787 A1 | 7/2017 | Lee et al. |
| 2018/0287657 A1 | 10/2018 | Rose et al. |
| 2019/0041846 A1 | 2/2019 | Cella et al. |

FOREIGN PATENT DOCUMENTS

| | | |
|---|---|---|
| EP | 1519253 A2 | 3/2005 |
| GB | 2338848 A | 12/1999 |
| GB | 2553299 A | 3/2018 |
| IN | 201621044490 A | 1/2017 |
| JP | 2009116420 A | 5/2009 |
| WO | 01/26068 A1 | 4/2001 |
| WO | 01/26335 A2 | 4/2001 |
| WO | 2014082074 A2 | 5/2014 |
| WO | 2016210388 A1 | 12/2016 |
| WO | 2017/184158 A1 | 10/2017 |
| WO | 2019028269 A2 | 2/2019 |

* cited by examiner

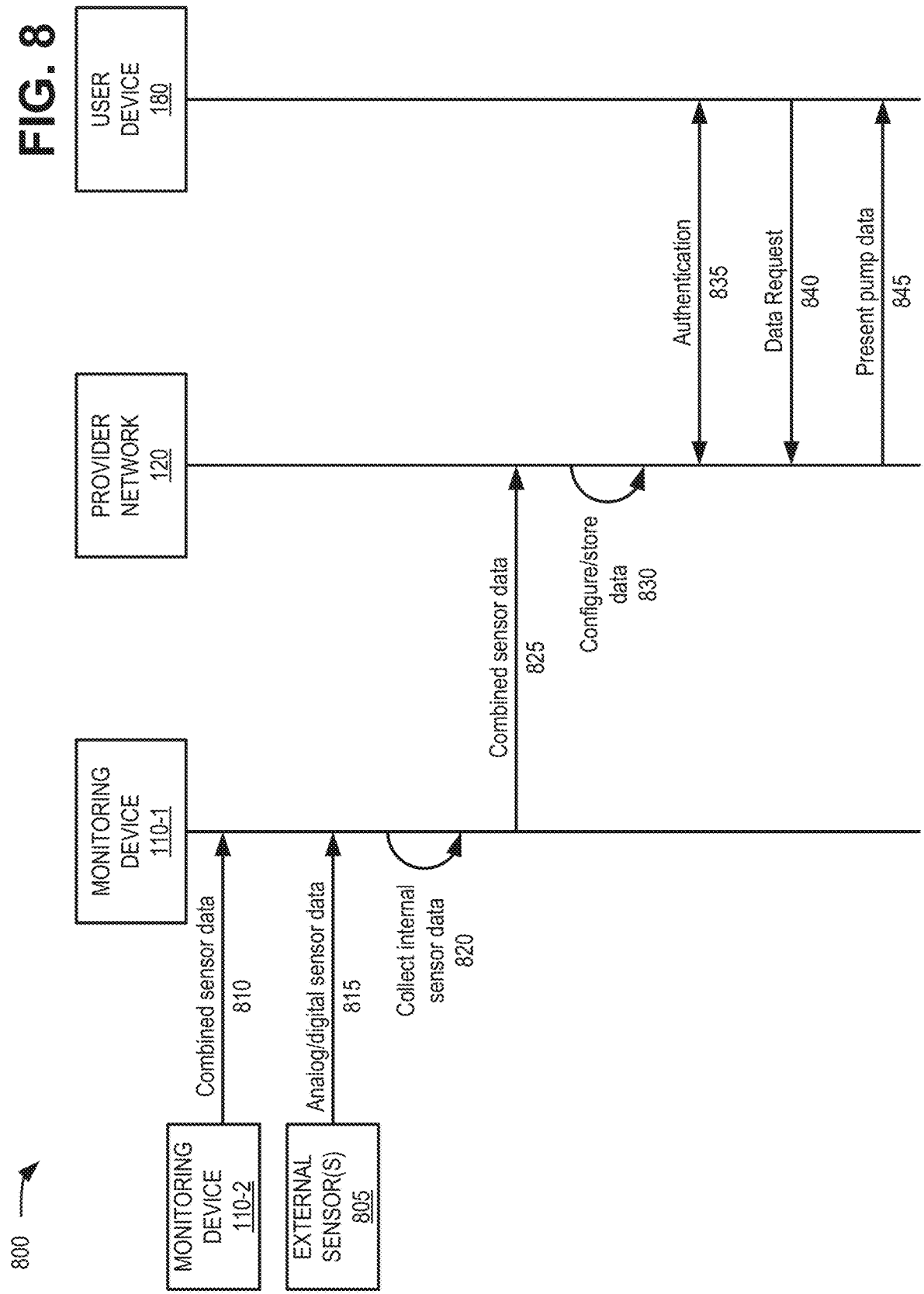

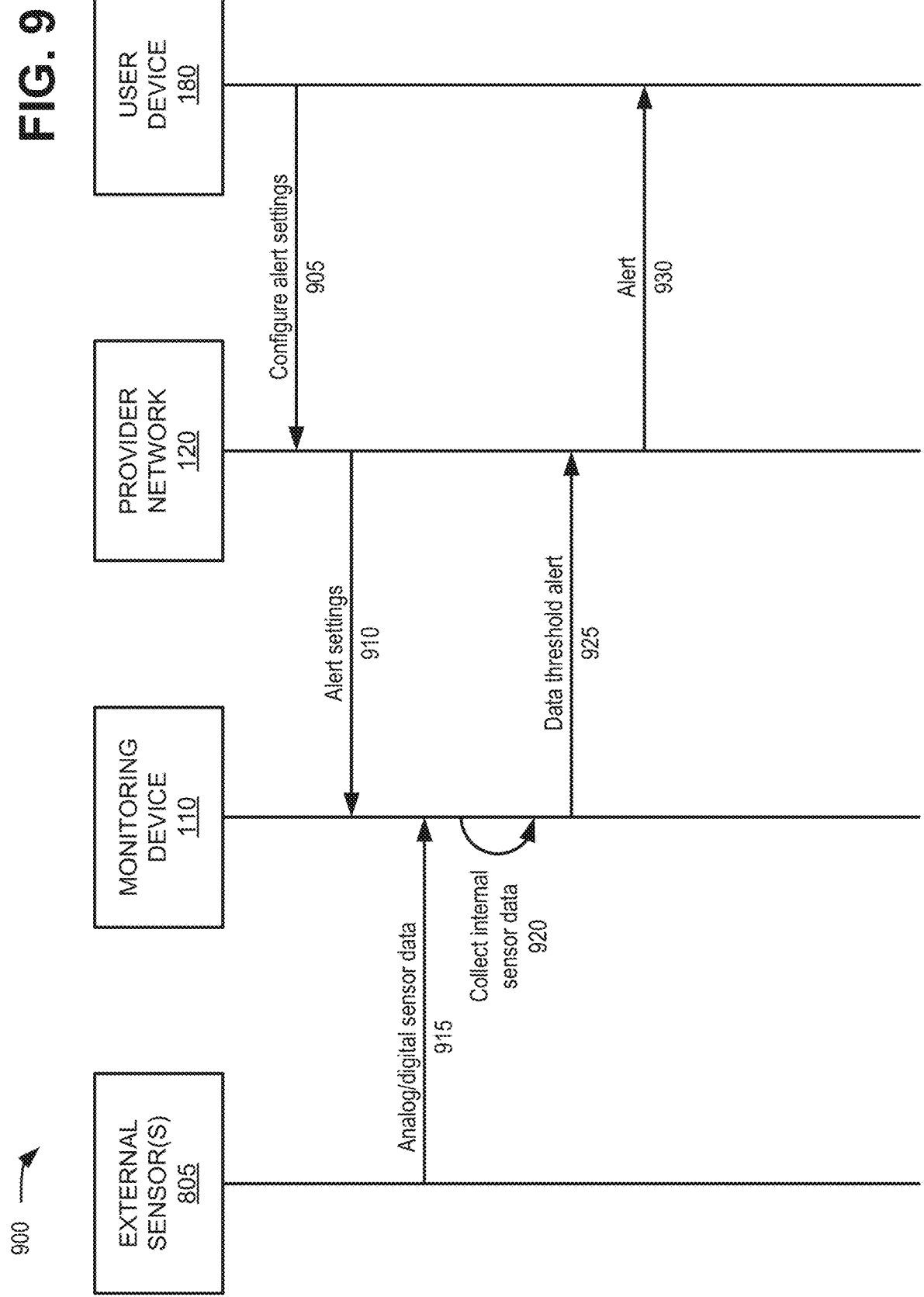

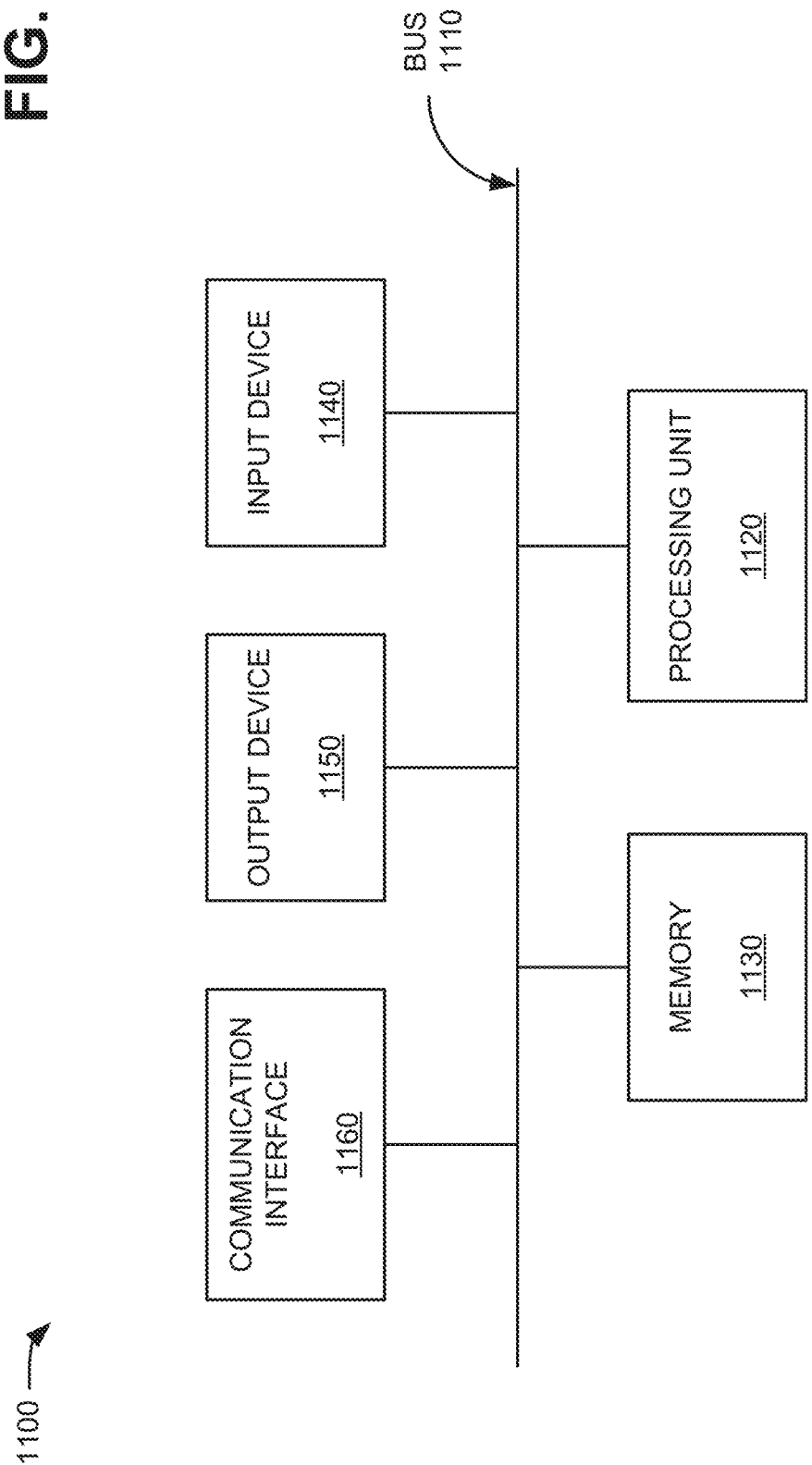

REMOTE EQUIPMENT MONITORING SYSTEM

CROSS-REFERENCE TO RELATED APPLICATION

This application claims priority under 35 U.S.C. § 119, based on U.S. Provisional Patent Application No. 62/840,025 filed Apr. 29, 2019, entitled "Remote Equipment Monitoring System," the disclosure of which is hereby incorporated by reference.

BACKGROUND OF THE INVENTION

Pumps have traditionally been monitored with two different techniques. With one of these techniques, pump data from pressure sensors, temperature sensors, and vibration sensors is sent to programmable logic controllers (PLC) and fed to supervisory control and data acquisition (SCADA) systems. These types of systems are not cost effective or practical for many types of pump installations and/or portable pumps.

With another technique, devices such as handheld vibration devices, temperature probes, pressure gauges, and the like, are used to perform periodic manual monitoring. Such periodic monitoring is typical for portable pumping systems and pumping systems without SCADA systems. This monitoring requires someone physically being present at the pump, the timing of which may not coincide with initial pump degradation or failure. Furthermore, periodic manual monitoring provides a measure of a pump condition only for the snap shot in time for which it is taken.

BRIEF DESCRIPTION OF THE DRAWINGS

FIG. 8 is a signal flow diagram illustrating typical communications in a portion of the environment of FIG. 1, according to an implementation;

FIG. 9 is a signal flow diagram illustrating alert communications in a portion of the environment of FIG. 1, according to another implementation;

FIG. 11 is a block diagram illustrating components of a network device or user device.

DETAILED DESCRIPTION OF THE PREFERRED EMBODIMENTS

The following detailed description refers to the accompanying drawings. The same reference numbers in different drawings may identify the same or similar elements. Also, the following detailed description does not limit the invention.

Systems and methods described herein provide an equipment monitoring system that gives pump users the ability to monitor pump health remotely. A monitoring device is provided as a single unit that is mechanically attached to an outside surface of the pump and detects vibration, temperature, and pump location. The monitoring device has the ability to accept hard wired inputs from external sensors/meters when the device is connected with continuous power. The monitoring device may use battery power, and can be converted to use continuous external power which gives the device more capabilities. Under external power, the monitoring device may conduct more frequent data sampling and data uploads, and communicate with attached external sensors and Modbus devices. Using communications through a provider network, users may establish threshold limits for vibration, temperature, and location. When the threshold limits are crossed, the system can push an alert message (e.g., via email or SMS message) to the pump user, distributor, manufacturer, etc.

In contrast with conventional pump monitors, systems and methods described herein provide a monitoring device configured for direct physical attachment, as a single unit, to pump equipment. The monitoring unit includes a sealed casing against dust or spray. The monitoring unit includes an internal battery that supports monitoring of internal vibration, temperature, and/or location sensors, along with data uploading over a cellular network. The monitoring unit provides a continuous power option to support additional monitoring of external sensors through hard-wired sensor ports. According to an implementation, the system may use vibration data from internal sensors to identify rotational speed of pump equipment. The monitoring device may use multiple types of wireless communications, including cellular broadband (for data uploads and configuration), personal area networks (PANs) (e.g., for alternative data uploading), and unlicensed radio spectrum (e.g., for inter-unit communications). Pump data from the monitoring device may be formatted, processed, and stored in a provider network. Authenticated users may access the pump data though a user device that connects to the provider network.

Figure 1:
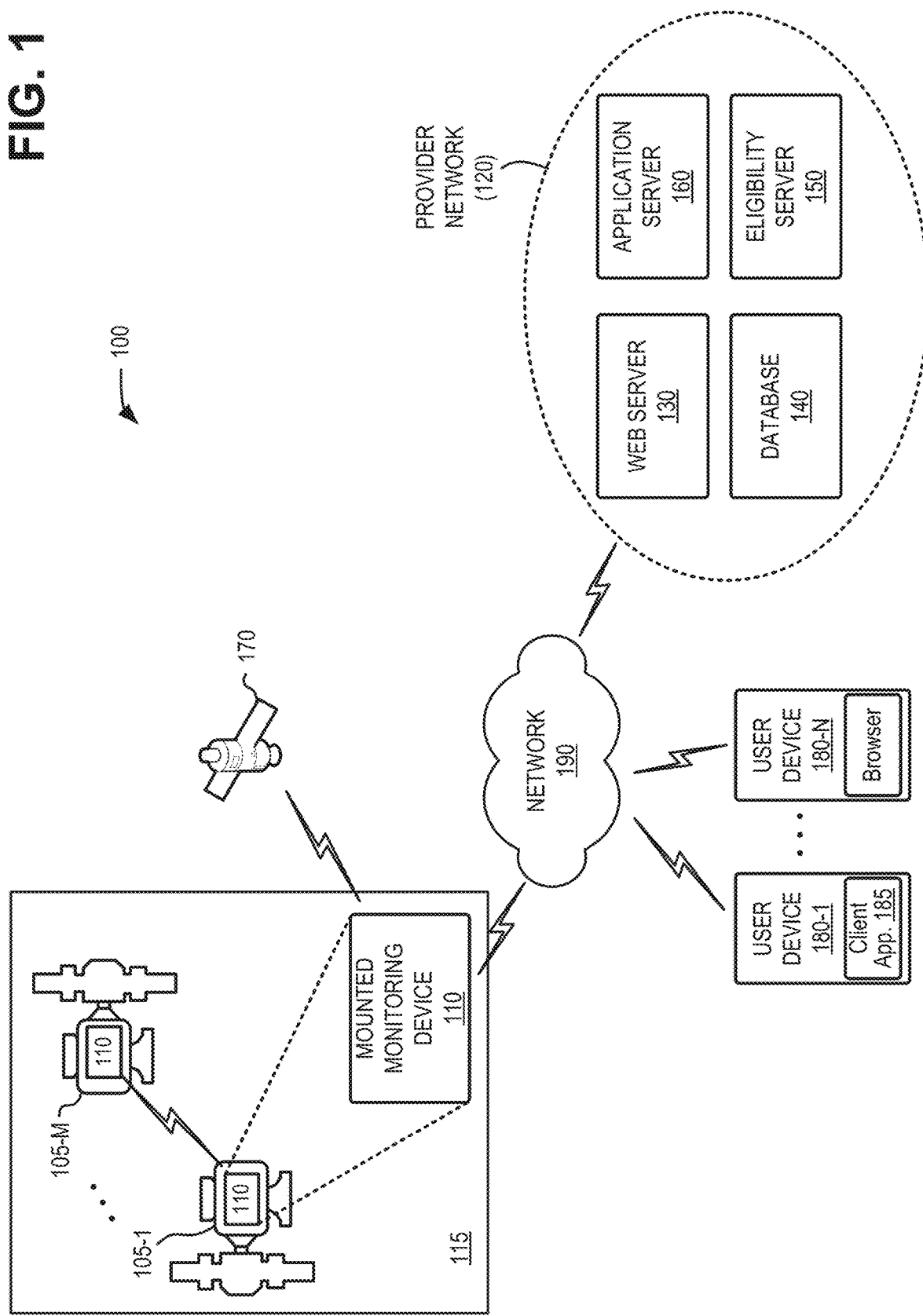
FIG. 1 is a diagram of a network environment in which systems and methods described here may be implemented.

FIG. 1 is a diagram illustrating an exemplary environment 100 in which systems and/or methods described herein may be implemented. As illustrated, environment 100 may include pump equipment 105-1 through 105-M (collectively and individually referred to herein as "pump equipment 105"). Each of pump equipment 105 may include a mounted monitoring device 110 (collectively referred to herein as "monitoring devices 110" and individually as "monitoring device 110"). Pump equipment 105 with mounted monitoring devices 110 may be distributed throughout customer premises 115, such as an industrial or agricultural environment. Environment 100 may also include a provider network 120 with a web server 130, a database 140, an eligibility server 150, and an application server 160; a global positioning system 170; user devices 180-1 through 180-N (collectively referred to herein as "user devices 180" and individually as "user device 180"), and a third-party device 180 interconnected by a network 190. Components of environment 100 may be connected via wired and/or wireless links.

Pump equipment 105 may include a pump, engine, electric motor, or any other piece of equipment (e.g., rotating equipment) the user wishes to monitor using vibration, temperature, and other sensors.

Monitoring device 110 may include an Internet of Things (IoT) device, a Machine Type Communication (MTC) device, a machine-to-machine (M2M) device, an enhanced MTC device (eMTC) (also known as Cat-M1), an end node employing Low Power Wide Area (LPWA) technology such as Narrow Band (NB) IoT (NB-IoT) technology, or some other type of wireless end node. According to various exemplary embodiments, monitoring device 110 may include hardware, such as a processor, application-specific integrated circuit (ASIC), a field-programmable gate array (FPGA), or a combination of hardware and software (e.g., a processor executing software) to execute various types of functions described further herein. As described further herein, monitoring device 110 may be attached to pump equipment 105; collect vibration, temperature, location, and other data; and forward collected data to provider network 120 for access to users.

Provider network 120 may include network devices, computing devices, and other equipment to provide services, including services for customers with monitoring devices 110. For example, devices in provider network 120 may supply backend services to user devices 180 for remotely monitoring pump equipment 105. Provider network 120 may include, for example, one or more private Internet Protocol (IP) networks that use a private IP address space. Provider network 120 may include a local area network (LAN), an intranet, a private wide area network (WAN), etc. According to an implementation, provider network 120 may use vendor-specific protocols to support IoT management. In another implementation, provider network 120 may include a hosting platform that provides an IoT data service. The IoT data service may include receiving packets that are transmitted by monitoring devices 110 and implementing models to collect, store, analyze, and/or present event data from monitoring devices 110. The hosting platform may also provide data-driven applications and/or analytics services for user devices 180 that owners of monitoring devices 110 may use. Examples of hosting platforms that may use different protocols and commands include Amazon® Web Services (AWS), Microsoft Azure®, IBM Watson®, Verizon® ThingSpace®, etc. Although shown as a single element in FIG. 1, provider network 120 may include a number of separate networks.

Web server 130 may include one or more network or computational devices to manage service requests from eligible user devices 180. In one implementation, web server 130 may provide an application (e.g., an event data management application) and/or instructions to user device 180 to enable user device 180 to receive and respond to information related to pump equipment 105. In another implementation, as described further herein, web server 130 may provide multiple types of browser-based user interfaces to facilitate individual pump monitoring, system monitoring, receive alerts, receive notifications, etc. Web server 130 may receive settings from user devices 180, may process/collate the received settings, and may forward the settings to application server 160 for implementation.

Database 140 may include one or more databases or other data structures to store data uploads from monitoring devices 110, reporting/monitoring configurations, device registrations (e.g., provided by user devices 180 via web server 130) and/or user registrations. In one implementation, database 140 may also store data retrieved from and/or used by eligibility server 150.

Eligibility server 150 may include one or more network or computational devices to provide backend support for authorizing monitoring devices 110 and/or user devices 180 to use provider network 120. For example, eligibility server 150 may perform a provisioning process for a monitoring device 110, including authentication, registration, and activation in network 190. Additionally, or alternatively, eligibility server 150 may store identification information for registered users and/or user devices 180. The information may be used to verify that a particular user/user device 180 has access to services and/or information provided by provider network 120. Upon verifying eligibility of a user/user device 110, eligibility server 150 may, for example, provide access to other devices in provider network 120.

Application server 160 may include one or more network or computational devices to perform services accessed through web server 130. For example, application server 160 may manage downloading applications provided to user devices 180, may process incoming data (e.g., from monitoring devices 110) for storage in database 140, and/or provide configuration information to monitoring devices 110. According to an implementation, application server 160 may use a series of APIs to send and receive data from monitoring devices 110.

Positioning system 170 may include one or more devices configured to provide location information to monitoring devices 110. In some implementations, location information may include, for example, GPS information or another form of global navigation satellite system (GNSS) information. In one implementation, positioning system 170 may include one or more cellular towers, wherein user devices may retrieve location information in the form of cellular tower triangulation information. Additionally, or alternatively, positioning system 170 may include a GPS satellite to determine a location of monitoring device 110.

User device 180 includes a device that has computational and wireless communication capabilities. User device 180 may be implemented as a mobile device, a portable device, a stationary device, a device operated by a user, or a device not operated by a user. For example, user device 180 may be implemented as a smartphone, a computer, a tablet, a wearable device, or some other type of wireless device. According to various exemplary embodiments, user device 180 may be configured to execute various types of software (e.g., applications, programs, etc.). As described further herein, user device 180 may download and/or register a client application 185. As described further herein, the client application 185 (or "app") may be designed to access, from provider network 120, data reported by monitoring devices 110. In another implementation, user device 180 may use a web browser to connect to web server 130 and perform similar functions of client application 185.

Network 190 may include one or more wired, wireless and/or optical networks that are capable of receiving and transmitting data, voice and/or video signals. For example, network 190 may include one or more access networks, IP multimedia subsystem (IMS) networks, core networks, or other networks. The access network may include one or more wireless networks and may include a number of transmission towers for receiving wireless signals and forwarding wireless signals toward the intended destinations. The access network may include a wireless communications network that connects subscribers (e.g., monitoring devices 110, user devices 180, etc.) to other portions of network 190 (e.g., the core network). In one example, the access network may include a long-term evolution (LTE) network. In other implementations, the access network may employ other cellular broadband network standards such as 3rd Generation Partnership Project (3GPP) 5G and future standards. Network 190 may further include one or more satellite networks, one or more packet switched networks, such as an IP-based network, a local area network (LAN), a wide area network (WAN), a personal area network (PAN) (e.g., a wireless PAN), a wireless local area network (WLAN), an intranet, the Internet, or another type of network that is capable of transmitting data.

In FIG. 1, the particular arrangement and number of components of environment 100 are illustrated for simplicity. In practice there may be more monitoring devices 110, provider networks 120, positioning systems 170, user devices 180, and/or networks 190. For example, there may be hundreds or thousands of monitoring devices 110.

Figure 2:
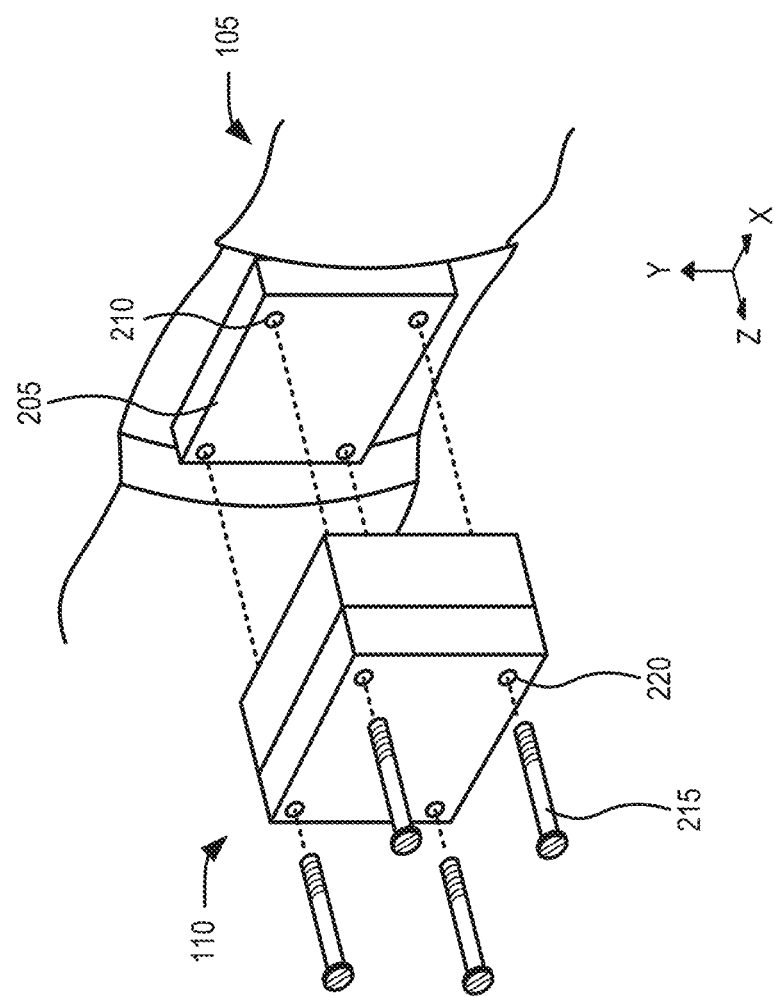
FIG. 2 is a schematic exploded view of a monitoring device and a portion of the pump equipment of FIG. 1.

FIG. 2 is a schematic exploded view of monitoring device 110 and a portion of pump equipment 105. As shown in FIG. 2, pump 105 may include a mounting surface 205 onto which monitoring device 110 may be attached. Mounting surface 205 may be a flat machined surface with mounting holes 210. In one implementation, mounting surface 205 may be on or part of the bearing housing of pump equipment 105. Mounting holes 210 may be configured to receive threaded mounting pins 215 (e.g., screws). In one implementation, mounting pins 215 may be threaded bolts separate from the housing of monitoring device 110. In another implementation, mounting pins 215 may be integrated into the housing of monitoring device 110. Mounting pins 215 may be inserted through holes 220 and secured in mounting holes 210 to attach monitoring device 110 to mounting surface 205. When attached to mounting surface 205, pump indicators, such a vibration and temperature, can be detected by sensors internal to monitoring device 110.

Figure 3:
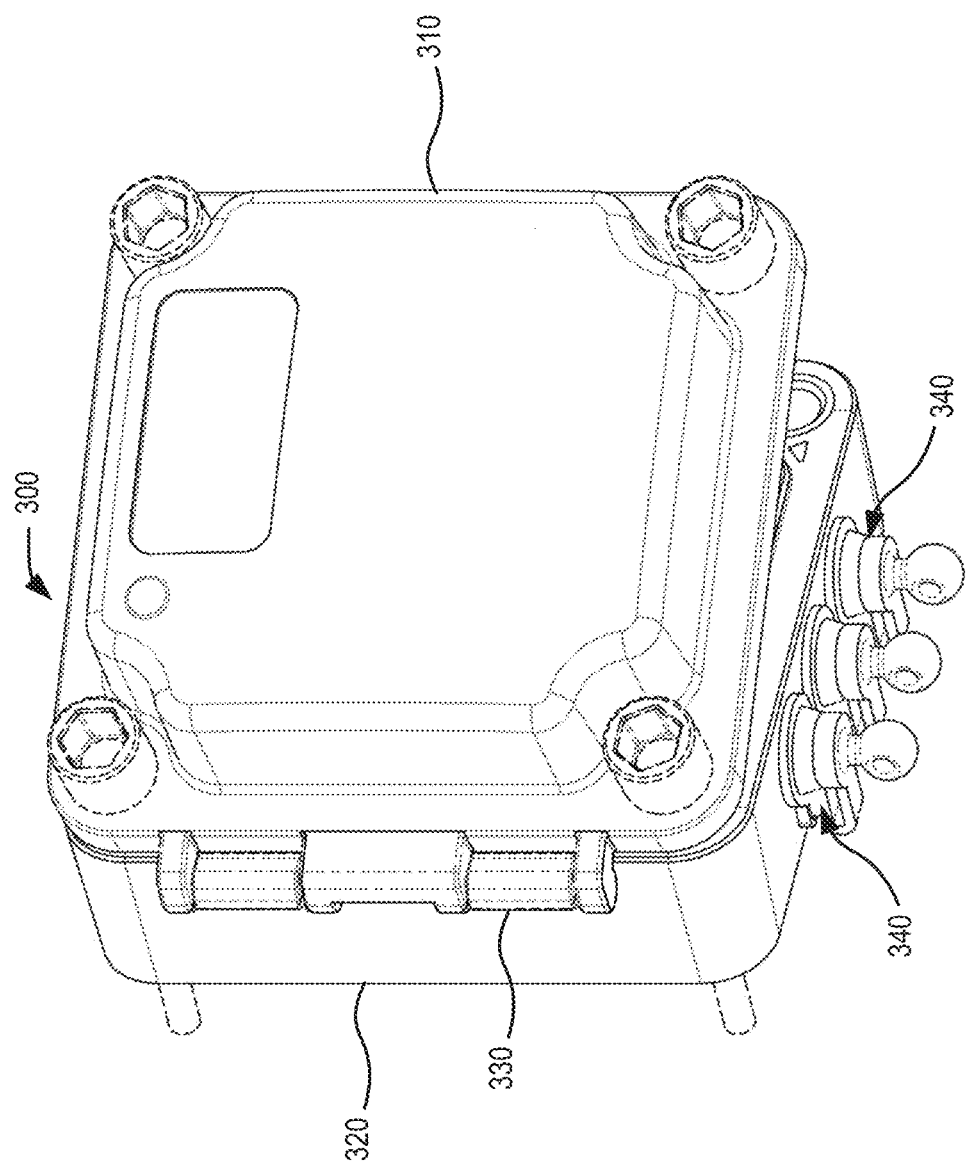
FIG. 3 is a front perspective view of the monitoring device of FIG. 1, shown with a partially open housing, according to an implementation.

FIG. 3 is a front perspective view of monitoring device 110, shown with a partially open housing, according to an implementation. Housing 300 of monitoring device 110 may include a front cover 310 and a base portion 320 connected by a hinge 330. In one implementation, housing 300 may provide a dust-resistant and water-spray resistant enclosure to protect internal components described further herein. In another implementation, housing 300 may meet one or more industrial standards for water-proof submersion. In one aspect, housing 300 may include integrated threaded mounting pins 215, such that monitoring device 110 may be attached to pump equipment 105 via the integrated screws.

Housing 300 may also include covered access ports 340, the covers of which may be removed/opened to provide access to connectors for external sensors. For example, connections internal to housing 300 may be accessed through covered access ports 340 (e.g., when opened) and used for wired connections to additional vibration sensors, pressure sensors, rotation speed sensors, temperature sensors, flow sensors, pressure sensors, or other external sensors. According to an implementation, one or more of covered access ports 340 may also provide for a DC power connection to an external power source. In another implementation, connectors may be located outside of housing 300. Housing 300 may be compact in size and structurally rigid (e.g., hard plastic material) to allow for mounting on pump equipment 105. In one implementation, housing may be less than 5 inches wide (e.g. x-axis of FIG. 2), 5 inches tall (e.g., y-axis), and 3 inches deep (z-axis).

Figure 4:
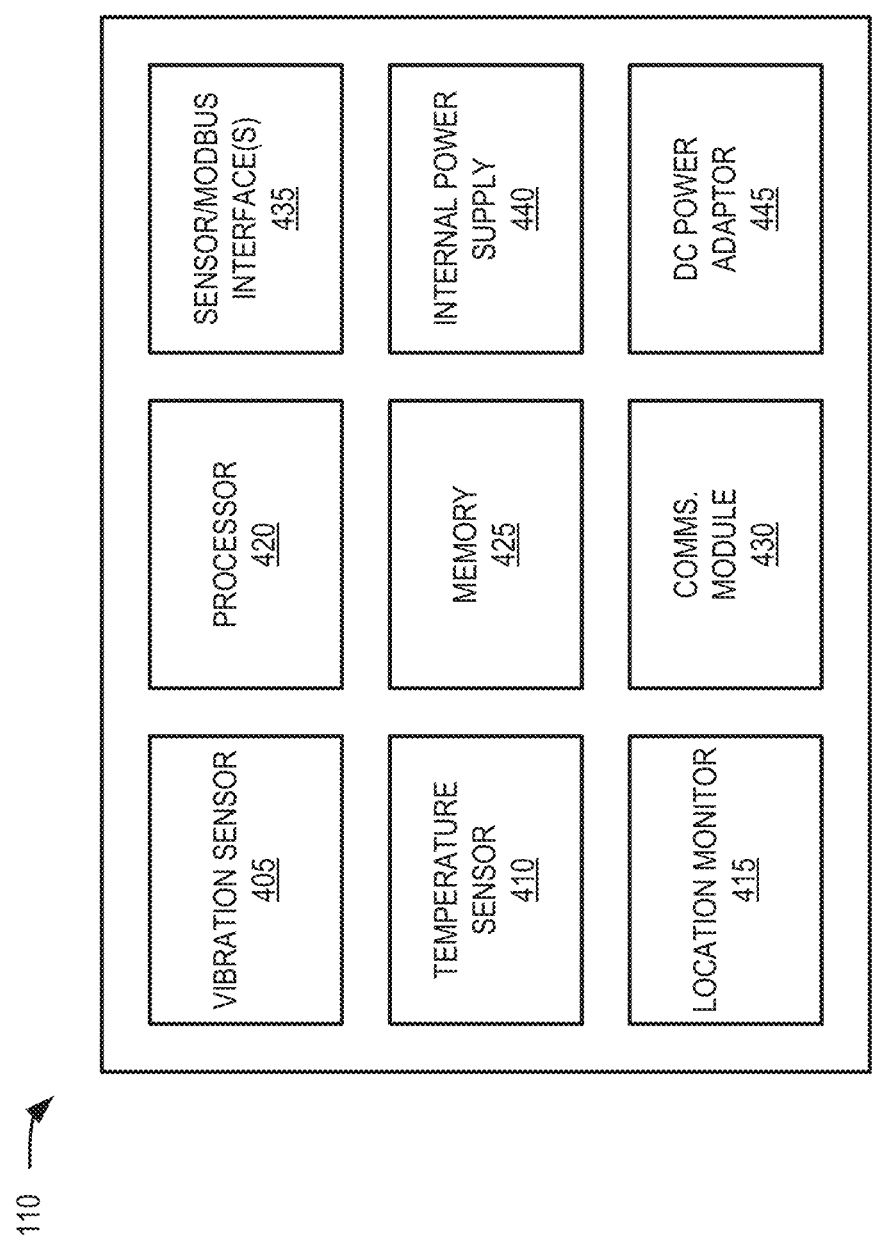
FIG. 4 is a block diagram illustrating internal components of the monitoring device of FIG. 1.

FIG. 4 is a block diagram of internal components of monitoring device 110. As shown in FIG. 4, monitoring device 110 may include a vibration sensor 405, a temperature sensor 410, a location monitor 415, a processor 420, a memory 425, a communications module 430, sensor/Modbus interfaces 435, an internal power supply 440, and power adaptor 445. The internal components may be enclosed, for example, within housing 300. According to an implementation, one or more components may be installed on a printed circuit board, an etched wiring board, or a printed circuit assembly.

Vibration sensor 405 may include accelerometers, signal amplifiers, and filters to detect and indicate sensed vibration in different directions. For example, vibration sensors 405 may include a set of three accelerometers to measure vibration along three respective axes (e.g., x-, y-, and z-axes of FIG. 2). In another implementation, vibration sensors 405 may measure vibration along two axes. According to one embodiment, the accelerometer may output a voltage proportional to the acceleration.

Temperature sensor 410 may include a sensor to detect a temperature within housing 300. The internal temperature of housing 300 may generally correspond to the temperature of the bearing housing of pump equipment 105. For example, changes in the bearing housing temperature will typically cause proportional temperature changes in the housing 300 of monitoring device 110. In one implementation, temperature sensor 410 may output an analog voltage value to processor 420 as a voltage output representing temperature (e.g., in degrees Fahrenheit or Celsius).

Location monitor 415 may communicate with positioning system 170 to detect a location of monitoring device 110. For example, location monitor 415 may include a location identification system (e.g., global positioning system (GPS) or another assisted location determining system).

Processor 420 may include one or multiple processors, microprocessors, data processors, co-processors, application specific integrated circuits (ASICs), controllers, programmable logic devices, chipsets, field-programmable gate arrays (FPGAs), application specific instruction-set processors (ASIPs), system-on-chips (SoCs), central processing units (CPUs) (e.g., one or multiple cores), microcontrollers, and/or some other type of component that interprets and/or executes instructions and/or data. Processor 420 may be implemented as hardware (e.g., a microprocessor, etc.), a combination of hardware and software (e.g., a SoC, an ASIC, etc.) and may include one or multiple memories (e.g., memory 425, cache, etc.).

Processor 420 may control the overall operation or a portion of operation(s) performed by monitoring device 110. Processor 420 may collect sample readings from vibration sensor 405, temperature sensor 410, location monitor 415, sensors connected to sensor/Modbus interfaces 435, internal power supply 440, and/or power adaptor 445. Processor 420 may determine sampling rates and available functions based on whether internal battery power or external power is used. Processor 420 may cause sample data to be sent to provider network 120 on a periodic basis. Processor 420 may also be programmed to detect if readings from any sensors exceed a predetermined threshold value and generate an alert signal when a threshold is exceeded. Functions of processor 420 are described further in connection with, for example, FIGS. 6-9.

Returning to FIG. 4, memory 425 includes one or multiple memories and/or one or multiple other types of storage mediums. For example, memory 425 may include random access memory (RAM), dynamic random access memory (DRAM), cache, read only memory (ROM), a programmable read only memory (PROM), a static random access memory (SRAM), a single in-line memory module (SIMM), a dual in-line memory module (DIMM), a flash memory (e.g., a NAND flash, a NOR flash, etc.), and/or some other type of memory. Alternatively, or additionally, memory 425 may include a Micro-Electromechanical System (MEMS)-based storage medium, and/or a nanotechnology-based storage medium. Memory 425 may store data (e.g., from vibration sensor 405, temperature sensor 410, location monitor 415, sensors connected to sensor/Modbus interfaces 435, internal power supply 440, and/or power adaptor 445), software, and/or instructions related to the operation of monitoring device 110.

Communications module 430 permits monitoring device 110 to communicate with other devices, networks, systems, devices, and/or the like. According to implementations described herein, communication module 430 includes multiple wireless interfaces. For example, communication module 430 may include multiple transmitters and receivers, or transceivers. Communication module 430 may include one or more antennas. For example, communication module 430 may include an array of antennas. Communication module 430 may operate according to a communication standard. Communication module 430 may include various processing logic or circuitry (e.g., multiplexing/de-multiplexing, filtering, amplifying, converting, error correction, etc.).

Figure 5:
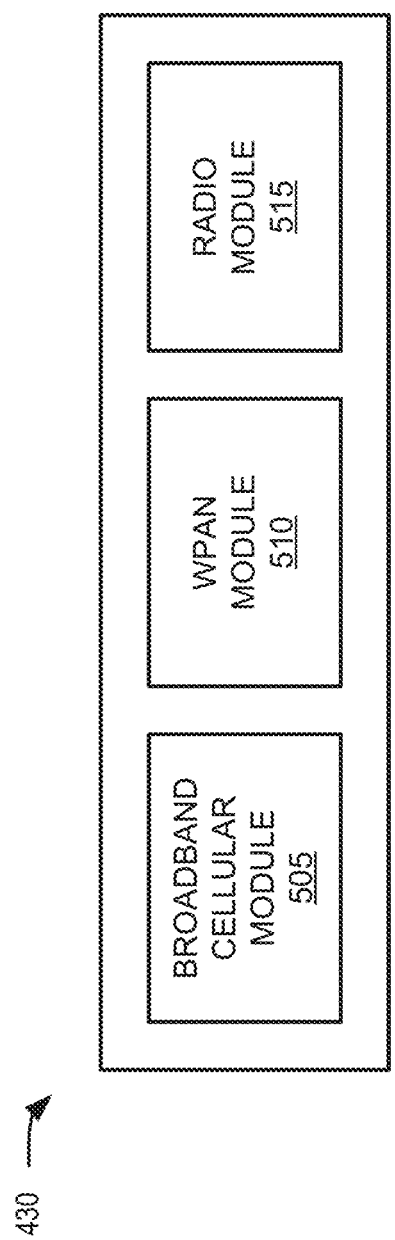
FIG. 5 is a block diagram illustrating components of the communications module of FIG. 4.

Communications module 430 is described further in connection with FIG. 5. As shown in FIG. 5, according to one implementation, communication module 430 may include a broadband cellular module 505, a wireless personal area network (WPAN) module 510, and a radio module 515.

Broadband cellular module 505 may include a cellular radio transceiver, which may operate according to any known cellular standard, including the standards known generally as Third Generation Partnership Project (3GPP) Fourth Generation (4G), 4.5 Generation (4.5G), or Fifth Generation (5G) mobile wireless standards. Broadband cellular module 505 may enable monitoring device 110 to conduct IoT communications with, for example, provider network 120.

WPAN module 510 may include a radio transceiver for a wireless personal area network (e.g., using IEEE 802.15 standards or Bluetooth®). WPAN module 510 may enable monitoring device 110 to transfer data to user device 180 when user device 180 is within a relatively short distance of monitoring device 110 (e.g., up to about 30 feet).

Radio module 515 may include a radio transceiver operating in an unlicensed spectrum (e.g., 900 MHz, 2.4 GHz). For example, radio module 515 may be based on an RJ45 Ethernet interface, a point-to-point radio interface, or a point-to-multipoint radio interface. Radio module 515 may enable communications between different monitoring devices 110, such as monitoring devices 110 in the same industrial, factory, or agricultural space over a range of thousands of feet.

Returning to FIG. 4, sensor/Modbus interface 435 may include one or more interfaces to receive (e.g., via wired connections when covers of covered access ports 340 are removed), analog or digital data from sensors and/or Modbus-enabled devices that are external to monitoring device 110. For example, sensor/Modbus interface 435 may include interfaces to accept hard-wired inputs from pump pressure sensors, flow sensors, rotation speed sensors, etc. According to an implementation, multiple sensor interfaces 435 (e.g., 3, 5, 8, etc.) may be used with monitoring device 110. According to another implementation, sensor/Modbus interface 435 may include a Modbus interface to enable monitoring device 110 to act as a Modbus master for other Modbus-enabled devices. For example, a Modbus connection may be used to allow monitoring device to receive and upload data from an engine (e.g., pump driver) associated with pump equipment 105.

Internal power supply 440 may include one or more batteries (e.g., a rechargeable battery, a replaceable battery, etc.) to power other components of monitoring device 110. Internal power supply 440 may include, for example, a conventional consumer-sized battery (e.g., size AA, 9-volt, etc.). In one implementation, internal power supply 440 may include a voltage monitor to measure a battery level (e.g., voltage of a battery).

External power adaptor 445 may include a connection for a direct current (DC) power source (e.g., from a storage device such as an external battery) or another power source. Generally, when an external power source (e.g., 9-30 volt DC) is connected to external power adaptor 445, monitoring device 110 operates using the external power source instead of internal power supply 440.

Although FIG. 4 shows exemplary components of monitoring device 110, in other implementations, monitoring device 110 may contain fewer, different, differently-arranged, or additional components than depicted in FIG. 4. Additionally, or alternatively, a component of monitoring device 110 may perform one or more other tasks described as being performed by another component of monitoring device 110.

Figure 6:
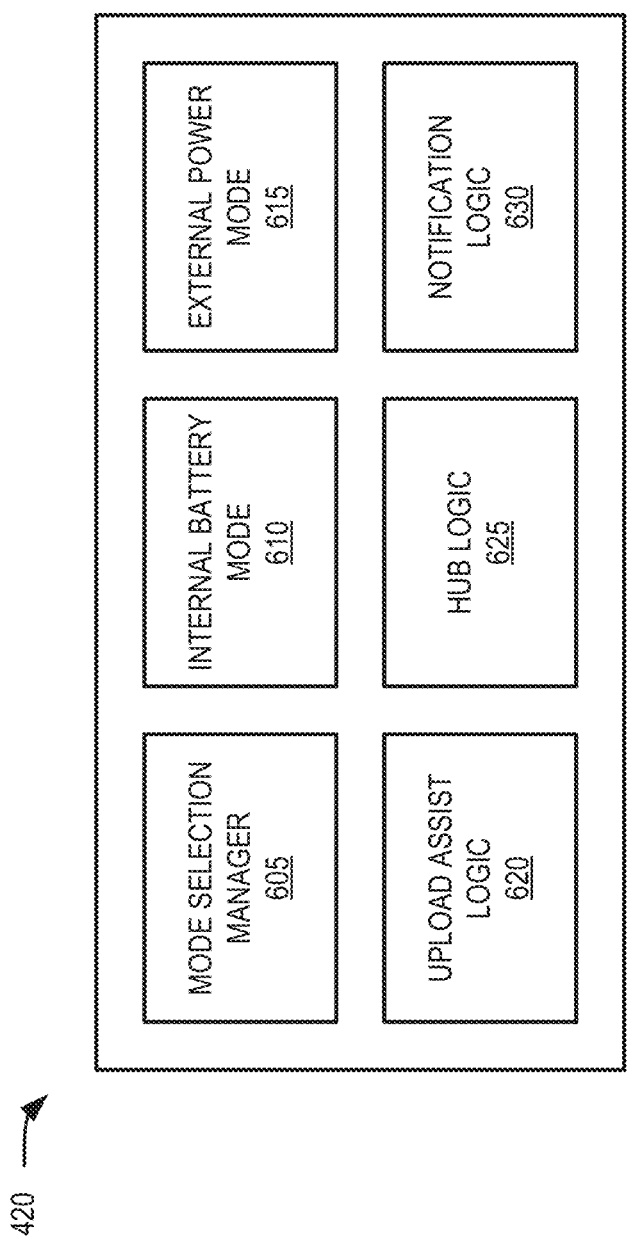
FIG. 6 is a diagram of exemplary logical components of the monitoring device of FIG. 1.

FIG. 6 is a diagram of exemplary logical components of monitoring device 110. As shown in FIG. 6, monitoring device 110 may include a mode selection manager 605, an internal battery mode 610, an external power mode 615, upload assist logic 620, hub logic 625, and notification logic 630. Functions of logical components of FIG. 6 may be performed, for example, by processor 420.

Mode selection manager 605 may detect what power source (e.g., internal battery 440 or external power through DC adaptor 445) is used by monitoring device 110 and select an appropriate operating mode for the current power source. Generally, mode selection manager 605 may select a mode with fewer features and less power consumption for internal battery power and a different mode with more features and greater power consumption for external power. For example, mode selection manager 605 may select internal battery mode 610 when only power from internal power supply 440 is available. Conversely, mode selection manager 605 may select external power mode 615 when an external power source in connected through adaptor 445.

Internal battery mode 610 may apply default or configurable settings for sensor data sampling and data uploads that minimize power consumption. For example, internal battery mode 610 may limit collection of sensor data to internal sensors (e.g., vibration sensor 405, temperature sensor 410, and location monitor 415) and/or processor clocks (e.g., for data time stamps). In one implementation, internal battery mode 610 may include a default configuration, such a four samples per hour of internal sensors only and two data uploads per day (e.g., via a broadband cellular connection). In another implementation, one or more settings for internal battery mode 610 may be configured by a user (e.g., via instructions provided to monitoring device 110 from provider network 120).

External power mode 615 may apply configurable settings for sensor data sampling and data uploads that optimize performance and features of monitoring device 110. For example, external power mode 615 may collect sensor data from both external sensors (e.g., connected via wires through covered access ports 340) and internal sensors (e.g., via vibration sensor 405, temperature sensor 410, and location monitor 415). In one implementation, external power mode 615 may include a more active default configuration compared with internal battery mode 610, such a twenty samples per hour of any internal and external sensors and eight data uploads per day (e.g., via a broadband cellular connection). In another implementation, one or more settings for external power mode 615 may be configured by a user (e.g., via instructions provided to monitoring device 110 from provider network 120).

Upload assist logic 620 may manage data uploads to provider network 120 based on settings in internal battery mode 610 or external power mode 615. For example, upload assist logic 620 may initiate a data session with application server 160 (e.g., via and broadband cellular module 505 and network 190) to perform an upload of data samples at periodic intervals governed by the currently selected mode. In another implementation, upload assist logic 620 may use WPAN module 510 to conduct data uploads (e.g., when a broadband cellular connection is not available). For example, upload assist logic 620 may detect, via a Bluetooth component, a user device 180 with a client application 185. If upload assist logic 620 detects stored data samples (e.g., from internal sensors or external sensors) that have not been uploaded from monitoring device 110, upload assist logic 620 may use WPAN module 510 to establish a wireless connection with user device 180. Upload assist logic 620 may upload the stored data samples to user device 180/client application 185, which may automatically forward the data samples to provider network 120 whenever user device 180 has a broadband cellular connection. According to one implementation, the data samples uploaded from monitoring device 110 to user device 180 are not configured for presentation by user device 180. Instead, user device 180/client application 185 may access provider network 120 for access to data from monitoring device 110. Thus, provider network 120 may maintain secure access to all uploaded data via eligibility server 150.

Hub logic 625 may manage communications and data exchanges among multiple monitoring devices 110. For example, hub logic 625 may use Radio module 515 to collect data from other monitoring devices 110 (e.g., monitoring devices 110 in the same factory) and provide the collected data (along with its own data) to provider network 120 using broadband cellular module 505 and network 190. In another implementation, hub logic 625 may use a point-to-point radio interface (e.g., 900 MHz radio), to receive data samples from other monitoring device 110 and temporarily store the other data samples along with locally collected data samples to form combined data samples. Hub logic 625 may send the combined data samples to provider network 120 at the appropriate periodic intervals (e.g., as indicted by internal battery mode 610 or external power mode 615). A monitoring device 110 in a group of monitoring devices may be configured as a hub by a user (e.g., based on location and/or signal quality). According to another implementation, hub logic 625 may self-select an acting hub among multiple monitoring devices 110. In still another implementation, hub logic 625 may perform a rotating hub selection process to distribute power consumption from hub activities among multiple monitoring devices 110.

Notification logic 630 may manage alert signals for detection of out-of-compliance behavior. For example, notification logic 630 may store or identify preset thresholds, which may be provided as part of a user configuration or factory defaults. Thresholds may include, for example, vibration deviations, temperature changes, temperature limits, pressure limits, flow rates, etc. In one implementation, the thresholds may be configured as part of internal battery mode 610 or external power mode 615. Notification logic 630 may determine when numerical values of each data samples from any of the internal sensors or external sensors exceed one of the corresponding thresholds. When a threshold is exceeded, notification logic 630 may send an alert signal to provider network 120. Provider network 120 may, in turn, provide an alert message (e.g., an SMS message, email, etc.) to a user.

Figure 7:
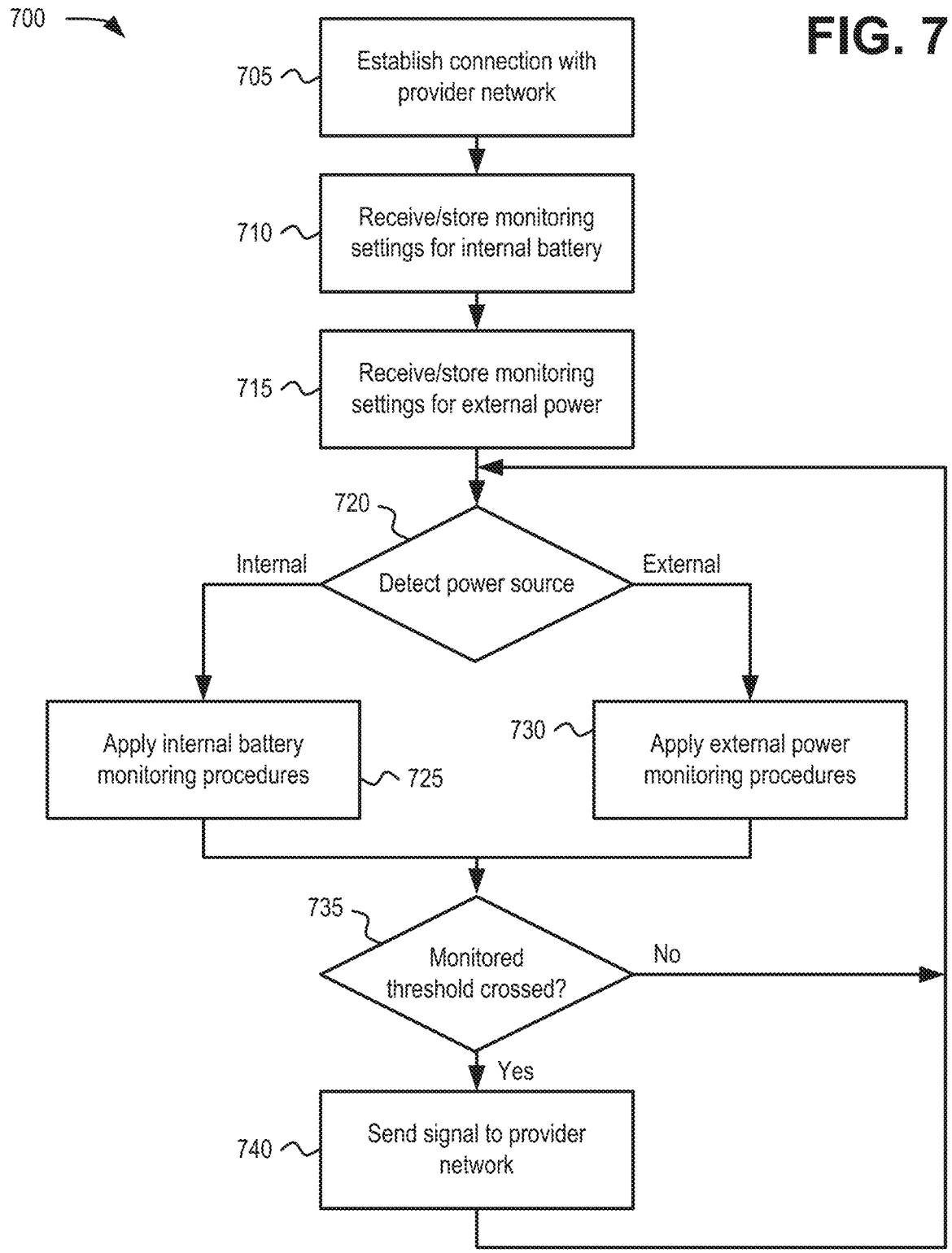
FIG. 7 is a flow diagram of a monitoring mode selection process, according to an implementation.

FIG. 7 is a flow diagram of a monitoring mode selection process 700. In one implementation, process 700 may be performed by processor 420 of monitoring device 110. In another implementation, process 700 may be performed by processor 420 in conjunction with one or more other components of monitoring device 110 and or provider network 120.

Process 700 may include establishing a wireless connection with a provider network (block 705). For example, monitoring device 110 may be configured with a URL, IP address, or another resource locator to enable monitoring device 110 to send information to and/or receive information from devices in provider network 120. Once activated on a cellular network (e.g., network 190), monitoring device 110 may establish communications with provider network 120 (e.g., application server 160).

Monitoring device 110 may receive and store settings for monitoring an internal battery (block 710). For example, in one implementation, a user using client application 185 on user device 180 may configure and/or modify settings for how monitoring device 110 acts when powered by internal power supply 440. Settings for monitoring internal power supply 440 may include setting for monitoring vibration (e.g., via vibration sensor 405), temperature (e.g., via temperature sensor 410), location (e.g., via location monitor 415), and battery voltage level. According to implementations described herein, settings for monitoring internal battery power may limit activity of monitoring device 110 to conserve battery power. For example, monitoring settings for internal battery power may disable communications with external sensors (e.g., sensor/Modbus interfaces 435), limit monitoring device 110 to a particular number of samples per hour (e.g., 2 to 6 samples per hour) from each internal sensor, and provide a limited number of data uploads per day (e.g., 1 to 4 uploads per day). Settings for monitoring internal battery power may further include alert settings, such as threshold levels for vibration, temperature, location and/or pump operating time. User configuration of settings for monitoring internal battery power may be provided to provider network 120 via authenticated users of user device. Provider network 120 (e.g., application server 160) in turn may provide the settings to monitoring device 110 via, for example, APIs over network 190. Monitoring device 110 may store the settings for monitoring internal battery power in a local memory (e.g. memory 425).

Monitoring device 110 may receive and store settings for monitoring external power (block 715). For example, similar to internal battery configurations described above, a user may use the client application 185 on user device 180 to configure and/or modify settings for how monitoring device 110 acts when powered through DC power adaptor 445. Settings for monitoring external power may include settings for internal sensors (e.g., via vibration sensor 405, temperature sensor 410, and location monitor 415), settings for external sensors (e.g., via sensor/Modbus interfaces 435), and data uploads. According to implementations described herein, settings for monitoring external power may provide increased functionality over the settings for monitoring internal battery power described above. For example, settings for monitoring external power may enable communications with external sensors (e.g., via sensor/Modbus interfaces 435) and sampling from internal sensors (e.g., vibration sensor 405, temperature sensor 410, and location monitor 415). Settings for monitoring external power may provide an increased amount of samples per hour (e.g., up to 20 samples per hour) from each internal sensor, and provide an increased number of data uploads per day (e.g., up to 12 uploads per day). Settings for monitoring external power may include alert settings, such as threshold levels for external sensors (e.g., pressure, flow, etc.), vibration, temperature, location, and/or pump operating time. Similar to communications for internal battery configurations described above, user configuration of settings for monitoring external power may be provided to provider network 120 via authenticated users of user device 180 and then provided to monitoring device 110 via network 190.

Monitoring device 110 may detect a power source as one of internal or external power (block 720). For example, monitoring device 110 may determine if an active power source is from internal power supply 440 or external power adaptor 445. If monitoring device 110 detects that internal power is being used (block 720—Internal), monitoring device 110 may apply the internal battery monitoring procedures (block 725). For example, monitoring device 100 may apply stored settings for monitoring internal battery power (e.g., described in connection with block 710 above) to monitor, collect, and report sample data.

If monitoring device 110 detects that external power is being used (block 720—External), monitoring device 110 may apply the external power monitoring procedures (block 730). For example, monitoring device 100 may apply stored settings for monitoring external power (e.g., described in connection with block 715 above) to monitor, collect, and report sample data.

Monitoring device 110 may detect if a threshold is crossed (block 720). For example, monitoring device 110 may apply thresholds for internal sensors only (e.g., for internal battery monitoring procedures) or for internal and external sensors (e.g., for external power monitoring procedures). In one implementation, monitoring device 110 may apply control logic to limit spurious notification signals. For example, monitoring device 110 may employ two or more thresholds (e.g., for the same sensor) to limit unnecessary alerts. For example, based on a vibration setting (e.g., as set by a user or a default threshold setting), monitoring device 110 may identify a low threshold (e.g., 5% below the vibration setting) and a high threshold (e.g., 5% above the vibration setting) with a hysteresis region in between the two thresholds. In another implementation, monitoring device 110 may be configured to require multiple consecutive high readings, for example, before generating an alert signal. Alternatively, control logic to limit spurious notifications may be applied at provider network 120.

When the monitoring device 110 detects that a monitored threshold is exceeded (block 735—Yes), monitoring device 110 may send a signal to the provider network (block 740). For example, monitoring device 110 may detect that a temperature threshold is exceeded and send an alert signal to application server 160 in provider network 120. Application server 160 may receive the alert signal and generate a message (e.g., a text message, email message, etc.) according to a corresponding user profile. If monitoring device 110 does not detect that a monitored threshold is exceeded (block 735—No), monitoring device 110 may continue to apply the appropriate monitoring settings based on the current power source for monitoring device 110.

FIG. 8 is a signal flow diagram illustrating typical communications in a portion 800 of environment 100 for using monitoring device 110 with DC power adaptor 445. As shown in FIG. 8, network environment portion 800 may include monitoring devices 110-1 and 110-2, provider network 120, user device 180, and external sensors 805. In the example of FIG. 8, assume monitoring devices 110-1 and 110-2 are attached to different pumps 105 in a single worksite and that monitoring device 110-1 acts as a hub for monitoring device 110-2. Some communications in FIG. 8 may correspond to block 730 of FIG. 7. Communications shown in FIG. 8 provide simplified illustrations of communications in portion 800 and are not intended to reflect every signal or communication exchanged between devices.

Monitoring device 110-1 may receive sensor data 805 from monitoring device 110-2. For example, using Radio module 515, monitoring device 110-2 may send local sampled data from internal sensors (e.g., vibration sensor 405, temperature sensor 410, and location monitor 415) and, if available, external sensor data. Sensor data 805 may be provided by monitoring device 110-2, for example, at generally the same intervals defined by the applicable internal battery monitoring procedures or external power monitoring procedures for monitoring device 110-2.

Monitoring device 110-1 may collect analog and/or digital sensor data 815 from external sensors 805. For example, monitoring device 110-1 may receive pressure and flow readings from pump sensors connected to sensor/Modbus interfaces 435. Monitoring device 110-1 may also collect internal sensor data 820 from internal sensors, such as local vibration sensor 405, temperature sensor 410, and location monitor 415.

Monitoring device 110-1 may compile sensor data 810, 815, and 820 as combined sensor data 825 and send combined sensor data 825 to provider network 120, thus providing a consolidated data channel for multiple sensors and/or pumps. Monitoring device 110-1 may send data at configured upload intervals using, for example, a broadband cellular connection. Provider network 120 (e.g., application server 160) may receive, process, and store 830 the combined sensor data 825 (e.g., store in database 140). Additionally, application server 160 may determine correlations to obtain additional information, such as pump rotational speed, based on combined sensor data 825.

After receiving combined sensor data 825, a user of user device 180 may initiate an authentication procedure 835 with provider network 120 to access stored data for pumps 105. In one implementation, authentication procedure 835 may be managed via client application 185 on user device 180. In another implementation, authentication procedure 835 may be managed via a web browser interface to solicit user credentials.

Assuming the user is authenticated, user device 180 may submit a data request 840 to provider network 120 to access data from monitoring devices 110. In response, provider network 120 may retrieve corresponding data stored in database 140, and provide the pump 105 data to user device 180 via, for example, web server 130 and/or the user application.

FIG. 9 is a signal flow diagram illustrating alert communications in a portion 900 of environment 100 for using monitoring device 110 with DC power adaptor 445. As shown in FIG. 9, network environment portion 900 may include monitoring device 110, provider network 120, user device 180, and external sensors 805. Communications shown in FIG. 9 provides simplified illustrations of communications in portion 900 and are not intended to reflect every signal or communication exchanged between devices.

Referring to FIG. 9, an authenticated user may use a client application on user device 180 to configure alert setting 905 for monitoring device(s) 110 on pump equipment 105. Alert settings may include, for example, (a) threshold values related to internal and external sensors for each monitoring device 110 and/or (b) contact information for automated alerts (e.g., e-mail address, phone numbers, etc.). Provider network 120 (e.g., application server 160) may forward some of the alert settings 910, such as the configuration thresholds (if applicable) to monitoring device 110. Monitoring device 110 may store the alert settings 910 (e.g., in memory 425). If external sensors 805 are connected to monitoring device 110, monitoring device 110 may collect analog and/or digital sensor data 915 from external sensors 805. Monitoring device 110-1 may also collect internal sensor data 920 from internal sensors, such as local vibration sensor 405, temperature sensor 410, and location monitor 415.

Monitoring device 110 may compare sensor data 915 and 920 with the stored alert settings 910. If monitoring device 110 identifies that a threshold had been exceeded for one or more sensors, monitoring device 110 may send a data threshold alert 925 to provider network 120. For example, monitoring device 110 may use a cellular connection to provide data threshold alert 925 to application server 160, without waiting for a configured data upload interval. In one implementation, the data threshold alert 925 may include the particular sensor data that triggered data threshold alert 925. In another implementation, data threshold alert 925 may include a full data upload of any unreported sensor data.

Upon receiving data threshold alert 925, provider network 120 (e.g., application server 160) may generate and send an alert message 930 in accordance with the configured alert settings 905. For example, application server 160 may generate and send an SMS message to one or more contacts associates with an account for monitoring device 110.

Although FIGS. 8 and 9 show exemplary communications for monitoring and alerts using monitoring device 110, in other implementations, fewer, different, or additional communications may be used. For example, if monitoring device 110 is not connected to external power, data from other monitoring devices and/or external sensors would not be included.

Figure 10A:
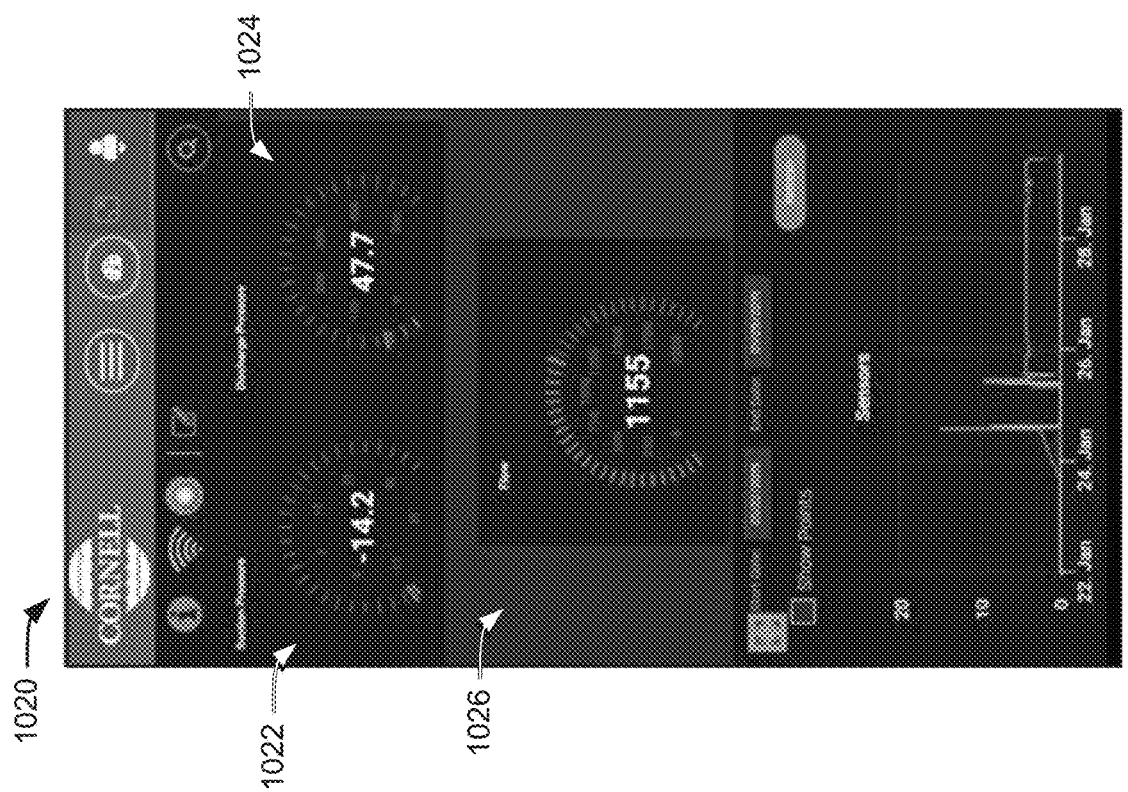
FIGS. 10A and 10B are illustrations of example user interfaces that may be presented via a client application, according to implementations described herein.
Figure 10B:
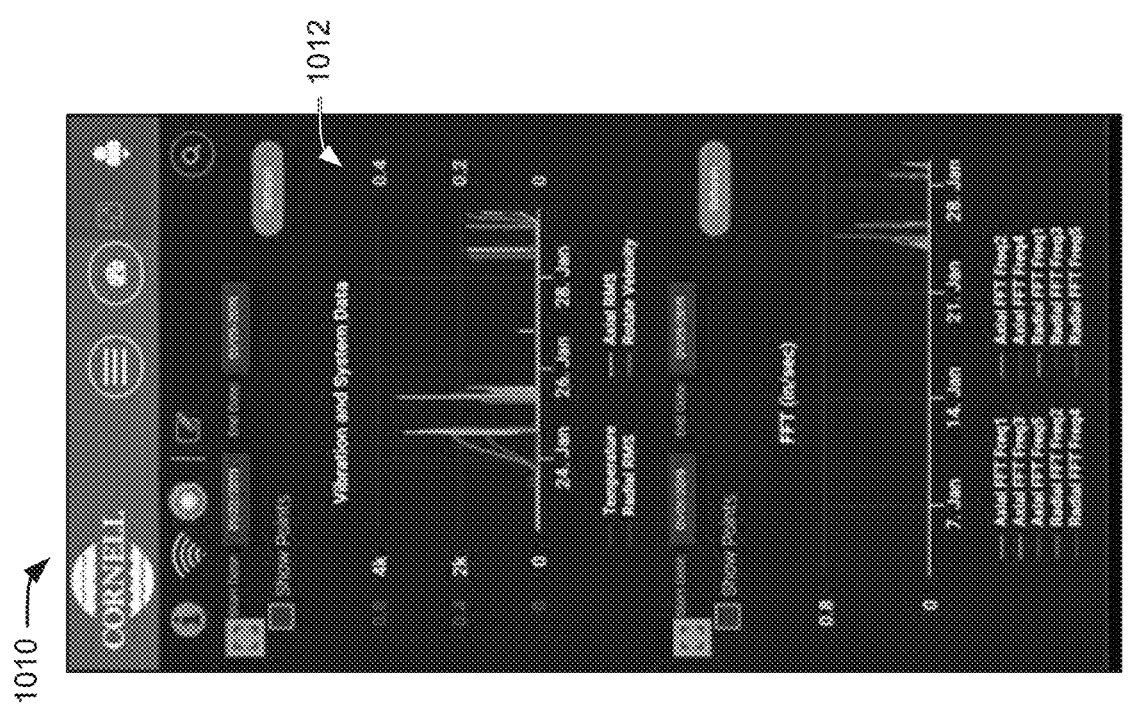

FIGS. 10A and 10B are examples of user interfaces 1010 and 1020 that may be presented on a user device 180. For example, user interfaces 1010 and 1020 may be presented on user device 180 (e.g., a smart phone or tablet device) executing client application 185. User interface 1010 of FIG. 10A may include a default user interface for monitoring device 110 operating in internal battery mode. User interface 1020 of FIG. 10B may include a user interface available when monitoring device 110 operates in external power mode.

Referring to FIG. 10A, for user interface 1010, client application 185 may retrieve data from provider network 120 to present to a user of user device 180. More particularly, user interface 1010 may present data from internal sensors of monitoring device 110, such as vibration sensor 405, temperature sensor 410, and location monitor 415. According to one implementation, user interface 1010 may also include pump rotational speed that is derived from rotation data. In the example of FIG. 10A, user interface 1010 may present data from vibration sensor 405 and temperature sensor 410 in a single graph 1012, where a user may provide input to select a time or date range for graph 1012 and have user interface 1010 selectively display different combinations of data segments (e.g., combinations of temperature, axial vibration, radial vibration, and/or rotational velocity).

Referring to FIG. 10B, for user interface 1020, client application 185 may retrieve data from provider network 120 to present to a user of user device 180. More particularly, user interface 1020 may present data from external sensors attached to monitoring device 110 (e.g., via wires through covered access ports 340), such as suction pressure sensors, discharge pressure sensors, flow sensors, etc. In the example of FIG. 10B, user interface 1020 may present a suction pressure graph 1022, a discharge pressure graph 1024, and a flow graph 1026. According to one implementation, ranges and/or scales for suction pressure graph 1022, a discharge pressure graph 1024, and a flow graph 1026 may be configurable to accommodate data from different pump types and pump sizes.

FIG. 11 is a diagram of exemplary components of a device 1100 that may correspond to web server 130, eligibility server 150, application server 160, or user device 180. As shown in FIG. 11, device 1100 may include a bus 1110, a processing unit 1120, a memory 1130, an input device 1140, an output device 1150, and a communication interface 1160.

Bus 1110 may permit communication among the components of device 1100. Processing unit 1120 may include one or more processors or microprocessors that interpret and execute instructions. In other implementations, processing unit 1120 may be implemented as or include one or more application specific integrated circuits (ASICs), field programmable gate arrays (FPGAs), or the like.

Memory 1130 may include a random access memory (RAM) or another type of dynamic storage device that stores information and instructions for execution by processing unit 1020, a read only memory (ROM) or another type of static storage device that stores static information and instructions for the processing unit 1120, and/or some other type of magnetic or optical recording medium and its corresponding drive for storing information and/or instructions.

Input device 1140 may include a device that permits an operator to input information to device 1100, such as a keyboard, a keypad, a mouse, a pen, a microphone, one or more biometric mechanisms, and the like. Output device 1150 may include a device that outputs information to the operator, such as a display, a speaker, etc.

Communication interface 1160 may include a transceiver that enables device 1100 to communicate with other devices and/or systems. For example, communication interface 1160 may include mechanisms for communicating with other devices, such as other computing devices. Each of such other devices may include its respective communication interface 1160 to achieve such communication.

As described herein, device 1100 may perform certain operations in response to processing unit 1120 executing software instructions contained in a computer-readable medium, such as memory 1130. A computer-readable medium may include a tangible, non-transitory memory device. A memory device may include space within a single physical memory device or spread across multiple physical memory devices. The software instructions may be read into memory 1130 from another computer-readable medium or from another device via communication interface 1160. The software instructions contained in memory 1130 may cause processing unit 1120 to perform processes described herein. Alternatively, hardwired circuitry may be used in place of or in combination with software instructions to implement processes described herein. Thus, implementations described herein are not limited to any specific combination of hardware circuitry and software.

Although FIG. 11 shows exemplary components of device 1100, in other implementations, device 1100 may contain fewer, different, differently-arranged, or additional components than depicted in FIG. 11. In still other implementations, a component of device 1100 may perform one or more other tasks described as being performed by another component of device 1100.

A device, system, and methods are provided for remotely monitoring pump equipment. A monitoring device is mechanically mounted to a pump. The monitoring device includes internal vibration, temperature, and location sensors to periodically monitor a pump and upload data samples via cellular connection to a provider network. The monitoring device additionally includes connections to external sensors that can be sampled and uploaded with the other data samples, when the monitoring device is connected to external power. Authenticated users access the pump data though a user device that connects to the provider network.

As set forth in this description and illustrated by the drawings, reference is made to "an exemplary embodiment," "an embodiment," "embodiments," etc., which may include a particular feature, structure or characteristic in connection with an embodiment(s). However, the use of the phrase or term "an embodiment," "embodiments," etc., in various places in the specification does not necessarily refer to all embodiments described, nor does it necessarily refer to the same embodiment, nor are separate or alternative embodiments necessarily mutually exclusive of other embodiment(s). The same applies to the term "implementation," "implementations," etc.

The foregoing description of embodiments provides illustration, but is not intended to be exhaustive or to limit the embodiments to the precise form disclosed. Accordingly, modifications to the embodiments described herein may be possible. For example, various modifications and changes may be made thereto, and additional embodiments may be implemented, without departing from the broader scope of the invention as set forth in the claims that follow. The description and drawings are accordingly to be regarded as illustrative rather than restrictive.

The terms "a," "an," and "the" are intended to be interpreted to include one or more items. Further, the phrase "based on" is intended to be interpreted as "based, at least in part, on," unless explicitly stated otherwise. The term "and/or" is intended to be interpreted to include any and all combinations of one or more of the associated items. The word "exemplary" is used herein to mean "serving as an example." Any embodiment or implementation described as "exemplary" is not necessarily to be construed as preferred or advantageous over other embodiments or implementations.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

No element, act, or instruction used in the description of the present application should be construed as critical or essential to the invention unless explicitly described as such.

What is claimed is:

1. A monitoring device for pump equipment, the monitoring device comprising:
   two or more internal sensors, the two or more internal sensors including a vibration sensor and a temperature sensor;
   a first communications interface for exchanging data with a provider network, wherein the first communications interface includes a cellular wireless interface;
   an internal battery;
   an external power adaptor;
   one or more connections for an external sensor;
   a memory configured to store instructions; and
   a processor configured to execute the instructions to:
      store, in the memory, a first set of data management settings for when the monitoring device is powered by the internal battery, the first set of data management settings including first sampling instructions for the two or more internal sensors,
      store, in the memory, a second set of data management settings for when the monitoring device is powered through the external power adaptor, the second set of data management settings including second sampling instructions for the two or more internal sensors and the external sensor,
      detect when the monitoring device is powered through the external power adaptor,
      apply the second set of data management settings, in response to the detecting, to collect data samples from at least one of the two or more internal sensors and the external sensor,
      store, in the memory, the data samples, and
      send, to the provider network, the data samples via the first communication interface and based on the second set of data management settings, when a cellular connection is available,
   wherein the monitoring device is configured for direct physical attachment to the pump equipment.

2. The monitoring device of claim 1, wherein the two or more internal sensors further include a location monitor, and
   wherein the first and second sets of data management settings each include sampling instructions for identifying a location of the monitoring device.

3. The monitoring device of claim 1, wherein, when applying the second set of data management settings, the processor is further configured to:
   obtain, at a first periodic interval, data samples from the two or more internal sensors and the external sensor; and
   establish, at a second periodic interval and via the first communications interface, a connection with the provider network.

4. The monitoring device of claim 3, wherein the second set of data management settings further includes different thresholds for the two or more internal sensors, and wherein the processor is further configured to execute the instructions to:
   determine when a numerical value of one of the data samples exceeds one of the different thresholds, and
   send, via the first communications interface, an alert signal to the provider network in response to the determining.

5. The monitoring device of claim 1, further comprising:
   a second communications interface for exchanging data with a local user device, wherein the second communications interface includes a wireless interface for a personal area network (PAN), and wherein the processor is further configured to execute the instructions to:
      when the cellular connection is not available, upload, to a user device executing a client application, the data samples via the second communications interface, wherein the data samples uploaded via the second communications interface are not configured for presentation by the user device.

6. The monitoring device of claim 1, further comprising:
a third communications interface for exchanging data with another monitoring device, wherein the third communications interface includes a point-to-point radio interface, wherein the processor is further configured to execute the instructions to:
receive, from the other monitoring device via the third communications interface, other data samples,
store, in the memory, the other data samples with the data samples to form combined data samples, and
send, via the first communications interface, the combined data samples to the provider network.

7. The monitoring device of claim 1, further comprising:
a housing enclosing the two or more internal sensors, the first communications interface, the one or more connections for the external sensor, the internal battery, the memory, and the processor, wherein the housing includes one or more covered access ports for the one or more connections for the external sensor.

8. The monitoring device of claim 1, wherein the one or more connections for an external sensor include connections for a vibration sensor, a suction pressure sensor, a discharge pressure sensor, or a flow sensor.

9. A system for monitoring pump equipment, the system comprising:
a monitoring device including:
two or more internal sensors, the two or more internal sensors including a vibration sensor and a temperature sensor,
a first communications interface for exchanging data with a provider network, wherein the first communications interface includes a cellular wireless interface,
an internal battery,
an external power adaptor,
one or more connections for an external sensor,
a first memory storing a first set of data management settings for when the monitoring device is powered by the internal battery and a second set of data management settings for when the monitoring device is powered through the external power adaptor, and
a first processor configured to:
receive, from the provider network and via the first communications interface, the second set of data management settings,
detect when the monitoring device is powered through the external power adaptor,
apply the second set of data management settings, in response to the detecting, to collect data samples from at least one of the two or more internal sensors and the external sensor, wherein the second set of data management settings includes sampling instructions for the two or more internal sensors and the external sensor,
store, in the first memory, the data samples, and
send, to the provider network, the data samples via the first communication interface and based on the second set of data management settings, when a cellular connection is available,
wherein the monitoring device is configured for direct physical attachment to the pump equipment.

10. The system of claim 9, further comprising:
a user device including:
a second memory to store instructions; and
a second processor configured to execute the instructions to:
receive, via a user interface, user input to define the second set of data management settings,
send, to the provider network, the user input, and
retrieve, from the provider network, monitoring data for the pump equipment based on the second set of data management settings.

11. The system of claim 10,
wherein the second processor of the user device is further configured to receive, from the provider network, rotational speed data derived from the vibration data.

12. The system of claim 10, further comprising:
a network device including:
a third memory to store instructions; and
a third processor configured to execute the instructions to:
store the monitoring data for the pump equipment,
authenticate a user of the user device, and
send, to the user device, the monitoring data for the pump equipment, after the authentication.

13. The system of claim 9, wherein the two or more internal sensors further include a location monitor, wherein the first and second sets of data management settings each include sampling instructions for identifying a location of the monitoring device.

14. The system of claim 9, wherein when applying the second set of data management settings, the first processor is further configured to:
obtain, at a first periodic interval, data samples from the two or more internal sensors and the external sensor; and
establish, at a second periodic interval and via the first communications interface, a connection with the provider network.

15. The system of claim 9, further comprising:
a housing enclosing the two or more internal sensors, the first communications interface, the one or more connections for the external sensor, the internal battery, the memory and the processor, wherein the housing includes one or more covered access ports for the one or more connections for the external sensor.

16. The system of claim 9, wherein the monitoring device further comprises:
a second communications interface for exchanging data with a user device, wherein the second communications interface includes a wireless interface for a personal area network (PAN), and wherein the first processor is further configured to execute the instructions to:
when the cellular connection is not available, upload, to the user device, the data samples via the second communications interface, wherein the data samples uploaded via the second communications interface are not configured for presentation by the user device,
wherein the second processor of the user device is further configured to receive the data samples from the monitoring device and forward the data samples to the provider network.

17. The system of claim 16, wherein the monitoring device further comprises:
a third communications interface for exchanging data with another monitoring device, wherein the third communications interface includes a point-to-point radio interface, wherein the first processor is further configured to execute the instructions to:
receive, from the other monitoring device via the third communications interface, other data samples,
store, in the memory, the other data samples with the data samples to form combined data samples, and
send, via the first communications interface, the combined data samples to the provider network.

18. A non-transitory computer-readable medium for a monitoring device, the non-transitory computer-readable medium containing instructions executable by at least one processor and comprising one or more instructions to cause the at least one processor to:
store, in a memory, a first set of data management settings for when the monitoring device is powered by an internal battery, the first set of data management settings including first sampling instructions for two or more internal sensors, the two or more internal sensors including a vibration sensor and a temperature sensor;
store, in the memory, a second set of data management settings for when the monitoring device is powered through an external power adaptor, the second set of data management settings including second sampling instructions for the two or more internal sensors and an external sensor that is connected to the monitoring device;
detect when the monitoring device is powered through the external power adaptor;
apply the second set of data management settings, in response to the detecting, to collect data samples from at least one of the two or more internal sensors and the external sensor;
store, in the memory, the data samples;
send, to a provider network, the data samples via a first communication interface and based on the second set of data management settings, when a cellular connection is available, and
send, to a user device, the data samples via a second communication interface and based on the second set of data management settings, when a cellular connection is not available.

19. The non-transitory computer-readable medium of claim 18, wherein the two or more internal sensors include a location monitor, wherein the first and second sets of data management settings each include sampling instructions for identifying a location of the monitoring device.

20. The non-transitory computer-readable medium of claim 18, wherein, when applying the second set of data management settings, the one or more instructions cause the at least one processor to:
obtain, at a first periodic interval, data samples from the two or more internal sensors and the external sensor; and
establish, at a second periodic interval and via the first communications interface, a connection with the provider network.

* * * * *